(12) United States Patent
Bodor et al.

US007888328B2

(10) Patent No.: US 7,888,328 B2
(45) Date of Patent: Feb. 15, 2011

(54) ORAL FORMULATIONS OF CLADRIBINE

(75) Inventors: Nicholas S. Bodor, Bal Harbour, FL (US); Yogesh Dandiker, Toronto (CA)

(73) Assignee: Ares Trading S.A., Aubonne (CH)

( * ) Notice: Subject to any disclaimer, the term of this patent is extended or adjusted under 35 U.S.C. 154(b) by 16 days.

(21) Appl. No.: 10/551,205

(22) PCT Filed: Mar. 26, 2004

(86) PCT No.: PCT/US2004/009387

§ 371 (c)(1),
(2), (4) Date: Nov. 14, 2006

(87) PCT Pub. No.: WO2004/087101

PCT Pub. Date: Oct. 14, 2004

(65) Prior Publication Data

US 2007/0197468 A1 Aug. 23, 2007

Related U.S. Application Data

(60) Provisional application No. 60/458,922, filed on Mar. 28, 2004, provisional application No. 60/484,756, filed on Jul. 2, 2003, provisional application No. 60/541,247, filed on Feb. 4, 2004.

(51) Int. Cl.
*A61K 31/7076* (2006.01)
*A61K 31/724* (2006.01)
(52) U.S. Cl. ............................. 514/46; 514/58
(58) Field of Classification Search .................. 514/46, 514/58
See application file for complete search history.

(56) References Cited

U.S. PATENT DOCUMENTS

| 3,459,731 | A | 8/1969 | Gramera et al. |
|---|---|---|---|
| 4,383,992 | A | 5/1983 | Lipari |
| 4,478,995 | A | 10/1984 | Shinoda et al. |
| 4,497,803 | A | 2/1985 | Harada et al. |
| 4,535,152 | A | 8/1985 | Szejtli et al. |
| 4,596,795 | A | 6/1986 | Pitha |
| 4,659,696 | A | 4/1987 | Hirai et al. |
| 4,727,064 | A | 2/1988 | Pitha |
| 4,764,604 | A | 8/1988 | Müller |
| 4,870,060 | A | 9/1989 | Müller |
| 5,106,837 | A | 4/1992 | Carson et al. |
| 5,310,732 | A | 5/1994 | Carson et al. |
| 5,401,724 | A | 3/1995 | Beutler |
| 5,424,296 | A | 6/1995 | Saven et al. |
| 5,506,214 | A | 4/1996 | Beutler |
| 5,510,336 | A | 4/1996 | Saven et al. |
| 6,174,873 | B1* | 1/2001 | Wrenn, Jr. ............ 514/45 |
| 6,194,395 | B1 | 2/2001 | Schultz et al. |
| 6,239,118 | B1 | 5/2001 | Schatz et al. |
| 6,407,079 | B1 | 6/2002 | Müller et al. |
| 6,699,849 | B1* | 3/2004 | Loftsson et al. ............ 514/58 |

FOREIGN PATENT DOCUMENTS

| DE | 31 18 218 A1 | 4/1982 |
|---|---|---|
| DE | 33 17 064 A1 | 11/1984 |
| EP | 0 094 157 A1 | 11/1983 |
| EP | 0 149 197 B1 | 7/1985 |
| EP | 0 197 571 A2 | 10/1986 |
| GB | 2 189 245 A | 10/1987 |
| WO | 90/12035 A1 | 10/1990 |
| WO | WO 99/42111 | 8/1999 |

OTHER PUBLICATIONS

Entry for liquid, Britannica Online Encyclopedia, http://www.search.eb.com/, accessed online on Dec. 31, 2008.*
Suzuki et al. Chem. Pharm. Bull., 1988, 36(2), p. 720-725.*
Suzuki et al. Chem. Pharm. Bull., 1993, 41(8), p. 1444-1447.*
Loftsson et al. Journal of Pharmaceutical Sciences, 2002, 91(11), p. 2307-2316.*
PCT International Preliminary Report on Patentability and Written Opinion for International Application No. PCT/US2004/009387, International filing date Mar. 26, 2004.
Gao, Shen, *New Dosage Form and New Technology of Modern Drugs*, first edition, Jan. 2002, Chapter 6, Section 3 (III) Procedures, p. 105, lines 25-29 (published by People's Military Medical Publisher), and English translation thereof.
Albertioni et al., "On the bioavailability of 2-chloro-2'-deoxyadenosine (CdA)", Eur J Clin Pharmacol., vol. 44, pp. 579-582, 1993, Springer-Verlag, Germany.
Ahn et al., "Chiral Recognition in Gas-Phase Cyclodextrin: Amino Acid Complexes-Is the Three Point Interaction Still Valid in the Gas Phase?", J Am Soc Mass Spectrom, vol. 12, pp. 278-287, 2001, Elsevier Science, Inc., US.
Bakthiar et al., "A study of the complexation between dimethyl-β-cyclodextrin and steroid hormones using electrospray ionization mass spectrometry", Rapid Communications in Mass Spectrometry, vol. 11, pp. 1478-1481, 1997, John Wiley And Sons Ltd, England.
Beutler et al., "The treatment of chronic progressive multiple sclerosis with cladribine", Proc. Natl. Acad. Sci. USA, Medical Sciences, vol. 93, pp. 1716-1720, 1996, National Academy of Sciences, US.
Cheng et al., "Measurement of chiral complexes of cyclodextrin and amino acids by electrospray ionization time-of-flight mass spectrometry", J. Mass Spectrom, vol. 36, pp. 834-836, 2001, John Wiley & Sons, Ltd., England.
Choi et al., "FT-Raman and FT-IR Spectra of the Non-steroidal Anti-inflammatory Drug Ketoprofen Included in Cyclodextrins", Analytical Sciences, vol. 17 Supplement, pp. i785-i788, 2001, The Japan Society for Analytical Chemistry, Japan.
Giordano et al., "Thermal analysis of cyclodextrins and their inclusion compounds", Thermochimica Acta 380, pp. 123-151, 2001, Elsevier Science B.V., The Netherlands.

(Continued)

*Primary Examiner*—Shaojia Anna Jiang
*Assistant Examiner*—Jonathan S Lau
(74) *Attorney, Agent, or Firm*—Buchanan Ingersoll & Rooney PC

(57) ABSTRACT

Provided are compositions of cladribine and cyclodextrin which are especially suited for the oral administration of cladribine.

55 Claims, 1 Drawing Sheet

OTHER PUBLICATIONS

Hwang et al., "Water Suppression That Works. Excitation Sculpting Using Arbitrary Waveforms and Pulsed Field Gradients", Journal of Magnetic Resonance, Series A, vol. 112, pp. 275-279, 1995, Academic Press, Inc., US.

Lamcharfi et al., "Electrospray Ionization Mass Spectrometry in Supramolecular Chemistry: Characterization of Non-covalent Cyclodextrin Complexes", Journal of Mass Spectrometry, vol. 31, pp. 982-986, 1996, John Wiley & Sons, Ltd., England.

Loftsson et al., "Pharmaceutical Applications of Cyclodextrin. 1. Drug Solubilization and Stabilization", Journal of Pharmaceutical Sciences, vol. 85, No. 10, pp. 1017-1025, 1996, American Pharmaceutical Association and the American Chemical Society, US.

Meier et al., "The Influence of β- and γ-Cyclodextrin Cavity Size on the Association Constant with Decanoate and Octanoate Anions", Journal of Inclusion Phenomena and Macrocyclic Chemistry, vol. 40, pp. 291-295, 2001, Kluwer Academic Publishers, The Netherlands.

Mura et al., "Interactions of ketoprofen and ibuprofen with β-cyclodextrins in solution and in the solid state", International Journal of Pharmaceutics, vol. 166, pp. 189-203, 1998, Elsevier Science B.V., The Netherlands.

Nolan et al., "Preparation of Vesicles and Nanoparticles of Amphiphilic Cyclodextrins Containing Labile Disulfide Bonds", Langmuir, vol. 19, pp. 4469-4472, 2003, American Chemical Society, US.

Ramanathan et al., "Electrospray Ionization Mass Spectrometric Study of Encapsulation of Amino Acids by Cyclodextrins", J. Am Soc Mass Spectrom, vol. 6, pp. 866-871, 1995, American Society for Mass Spectrometry, US.

Redenti et al., "Raman and Solid State $^{13}$C-NMR Investigation of the Structure of the 1 : 1 Amorphous Piroxicam : β-Cyclodextrin Inclusion Compound", Biospectroscopy, vol. 5, pp. 243-251, 1999, John Wiley & Sons, Inc., US.

Sipe et al., "Cladribine in treatment of chronic progressive multiple sclerosis", The Lancet, vol. 344, pp. 9-13, 1994, Lancet Publishing Group, England.

Szejtli, "Introduction and General Overview of Cyclodextrin Chemistry", Chem. Rev., vol. 98, pp. 1743-1753, 1998, American Chemical Society, US.

Uekama et al., "Cyclodextrin Drug Carrier Systems", Chem. Rev., vol. 98, pp. 2045-2076, 1998, American Chemical Society, US.

Uekama et al., "Peracylated β-Cyclodextrins as Novel Sustained-release Carriers for a Water-soluble Drug, Molsidomine", J. Pharm. Pharmacol., vol. 46, pp. 714-717, 1994, Pharmaceutical Press, England.

Taddei et al., "Influence of Environment on Piroxicam Polymorphism: Vibrational Spectroscopic Study", Biopolymers (Biospectroscopy), vol. 62, pp. 68-78, 2001, John Wiley & Sons, Inc., US.

Tarasiuk et al., "*Stability of 2-Chloro-2'-Deoxyadenosine at Various pH and Temperature*", Archivum Immunologiae et Therapiae Experimentalis, vol. 42, pp. 13-15, 1994, published by Birkhauser Publishers Ltd., Basel, Switzerland.

Romine et al., "*A Double-Blind, Placebo-Controlled, Randomized Trial of Cladribine in Relapsing-Remitting Multiple Sclerosis*", Proceedings of the Association of American Physicians, vol. 111, No. 1, pp. 35-44, 1999, published by Blackwell Publishing, Malden, MA.

Tortorella et al., Current Opinion on Investigational Drugs, 2(12), pp. 1751-1756, 2001, published by PharmaPress Ltd., London, GB.

Selby et al., "*Safety and Tolerability of Subcutaneous Cladribine Therapy in Progressive Multiple Sclerosis*", Can. J. Neurol Sci., vol. 25, pp. 295-299, 1998, published by Canadian Journal of Neurological Science, Calgary, Canada.

Rice et al., "*Cladribine and progressive MS Clinical and MRI outcomes of a multicenter controlled trial*", Neurology, vol. 54, pp. 1145-1155, 2000, published by Lippincott Williams and Wilkins, Hagerstown, MD.

Liliemark et al., "*On the Bioavailability of Oral and Subcutaneous 2-Chloro-2'-Deoxyadenosine in Humans: Alternative Routes of Administration*", Journal of Clinical Oncology, vol. 10, No. 10, pp. 1514-1518, 1992, published by American Society of Clinicial Oncology, Alexandria, VA.

Karlsson et al., "*Oral cladribine for B-cell chronic lymphocytic leukaemia: report of a phase II trial with a 3-d, 3-weekly schedule in untreated and pretreated patients, and a long-term follow-up of 126 previously untreated patients*", British Journal of Haematology, vol. 116, pp. 538-548, 2002, published by Blackwell Science Ltd., Oxford, UK.

Liliemark, "*The Clinical Pharmacokinetics of Cladribine*" Clin. Pharmacokinet, vol. 32 (2), pp. 120-131, 1997, published by Adis International Limited, Wolters Kluwer Health, Yardley, PA.

Nakai et al., "*Effects of Grinding on the Physical and Chemical Properties of Crystalline Medicinals with Microcrystalline Cellulose V: Comparison with Tri-O-methyl-β-cyclodextrin Ground Mixtures*", Chem. Pharm. Bulletin, vol. 28(5), pp. 1552-1558, 1980, published by Pharmaceutical Society of Japan, Tokyo, Japan.

Saenger, "*Clyclodextrin Inclusion Compounds in Research and Industry*", Angew. Chem. Int. Ed. Engl., vol. 19, pp. 344-362, 1980, published by Verlag Chemie, GmbH, Weinheim, Germany.

Tang et al., "*Design of Freeze-Drying Processes for Pharmaceuticals: Practical Advice*", Pharmaceutical Research, vol. 21, No. 2, pp. 191-200, 2004, Springer, The Netherlands.

Van Axel Castelli et al. "Characterisation of an Inclusion Complex Between Cladribine and 2-Hydroxypropyl-β-Cyclodextrin," *J. Pharm. Sci.*, vol. 97, No. 9, Sep. 2008, pp. 3897-3906, Wiley InterScience and the American Pharmacists Association, US.

Drugs.com, "Oral Investigational Treatment Cladribine Tablets for Multiple Sclerosis Significantly Reduced Relapse Rate in Phase III Pivotal Trial," accessed online Feb. 3, 2009, at http://www.drugs.com/clinical_trials/oral-investigational-cladribine-multiple-sclerosis.

"Serono's Oral Cladribine for the Treatment of Multiple Sclerosis Awarded Fast Track Status by FDA", accessed online Feb. 3, 2009 at http://prnewswire.com.

Merck Serono News Release, "Two-year Phase III Data Presented at AAN 61st Annual Meeting Show Positive Outcome of Cladribine Tablets in Patients with Multiple Sclerosis", Apr. 29/30, 2009, available online.

* cited by examiner

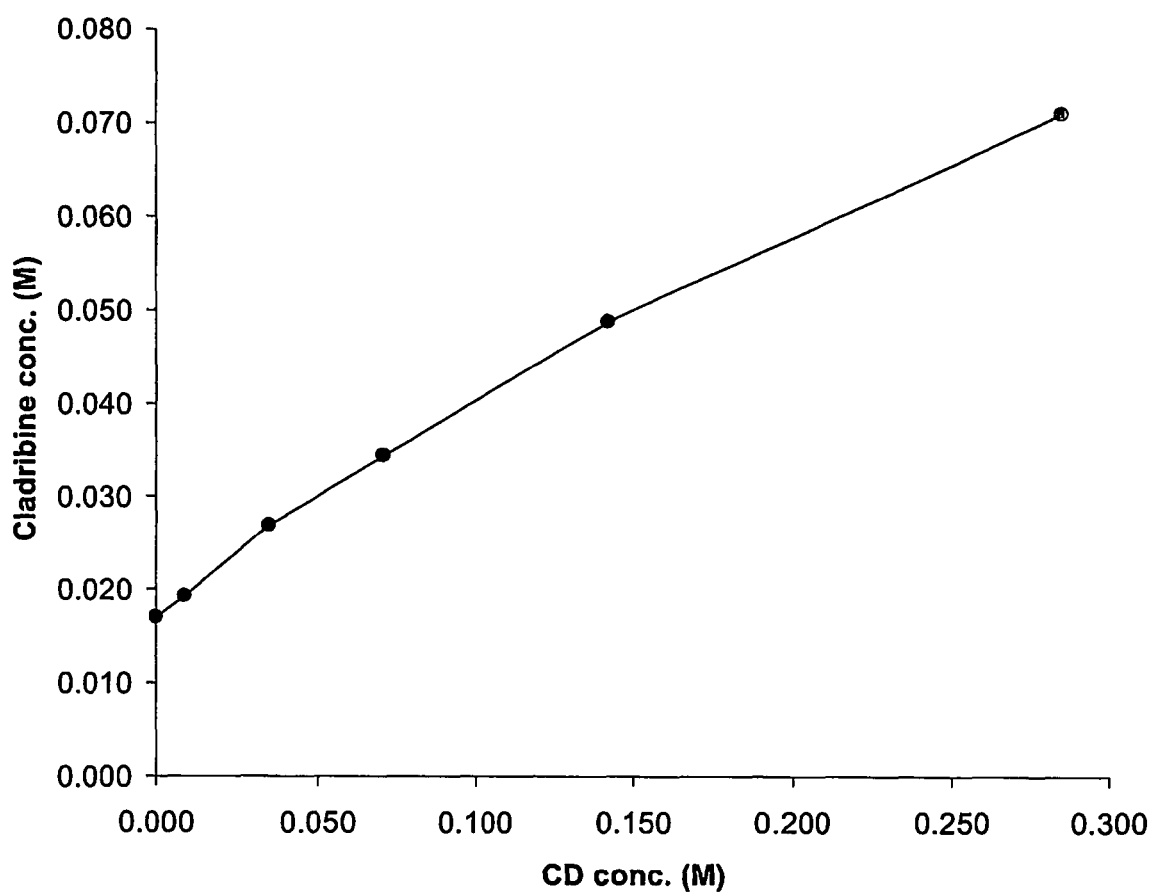

ORAL FORMULATIONS OF CLADRIBINE

CROSS-REFERENCE TO EARLIER APPLICATIONS

This application is the U.S. national stage of International Application No. PCT/US2004/009387, file Mar. 26, 2004, which claims benefit under 35 U.S.C. §119(e) of U.S. Provisional Application No. 60/458,922, filed Mar. 28, 2003; of U.S. Provisional Application No. 60/484,756, file Jul. 2, 2003; and of U.S. Provisional Application No. 60/541,247, filed Feb. 4, 2004, all of said applications being hereby incorporated by reference herein in their entireties and relied upon.

FIELD OF THE INVENTION

The invention relates to a composition comprising a complex cladribine-cyclodextrin complex formulated into a solid oral dosage form and to a method for enhancing the oral bioavailability of cladribine.

BACKGROUND OF THE INVENTION

Cladribine, which is an acid-labile drug, has the chemical structure as set forth below:

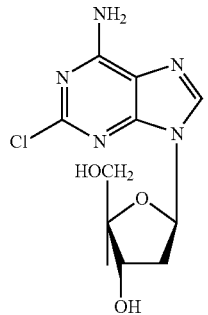

It is also known as 2-chloro-2'-deoxyadenosine or 2-CdA. Cladribine exists as a white, nonhydroscopic, crystalline powder, consisting of individual crystals and of crystalline aggregates.

Cladribine is an antimetabolite which has use in the treatment of lymphoproliferative disorders. It has been used to treat experimental leukemias such as L1210 and clinically for hairy cell leukemia and chronic lymphocytic leukemia as well as Waldenstrom's macroglobulinaemia. It has also been used as an immunosuppressive agent and as a modality for the treatment of a variety of autoimmune conditions including rheumatoid arthritis, inflammatory bowel disease (e.g., Crohn's disease, ulcerative colitis) and multiple sclerosis (see e.g., J. Liliemark, *Clin. Parmacokinet*, 32(2): 120-131, 1997). It has also been investigated, either experimentally or clinically in, for example, lymphomas, Langerhan's cell histiocytosis, lupus erythematosus, chronic plaque psoriasis, Sezary syndrome, Bing-Neel syndrome, recurrent glioma, and solid tumors.

Oral delivery of drugs is often preferred to parenteral delivery for a variety of reasons, foremost patient compliance, or for cost or therapeutic considerations. Patient compliance is enhanced insofar as oral dosage forms alleviate repeated health care provider visits, or the discomfort of injections or prolonged infusion times associated with some active drugs. At a time of escalating health care costs, the reduced costs associated with oral administration versus parenteral administration costs gain importance. The cost of parenteral administration is much higher due to the requirement that a health care professional administer the cladribine in the health care provider setting, which also includes all attendant costs associated with such administration. Furthermore, in certain instances, therapeutic considerations such as the need for a slow release of cladribine over a prolonged period of time may be practically met only by oral or transmucosal delivery.

However, to date the oral delivery of cladribine has been plagued by low bioavailability (see, e.g., J. Liliemark et al., *J. Clin. Oncol.*, 10(10): 1514-1518, 1992), and suboptimal interpatient variation (see, e.g., J. Liliemark, *Clin. Pharmacokinet*, 32 (2): 120-131, 1997). See also, A. Tarasuik, et al. reporting poor absorption and pH dependent lability (*Arch. Immunol.* et *Therapiae Exper.*, 42: 13-15, 1994).

Cyclodextrins are cyclic oligosaccharides composed of cyclic α-(1→4) linked D-glucopyranose units. Cyclodextrins with six to eight units have been named α-, β- and γ-cyclodextrin, respectively. The number of units determines the size of the cone-shaped cavity which characterizes cyclodextrins and into which drugs may be included to form stable complexes. A number of derivatives of α-, β- and γ-cyclodextrin are known in which one or more hydroxyl groups is/are replaced with ether groups or other radicals. These compounds are thus known complexing agents and have been previously used in the pharmaceutical field to form inclusion complexes with water-insoluble drugs and to thus solubilize them in aqueous media.

Recently, Schultz et al., in U.S. Pat. No. 6,194,395 B1, have described complexing and solubilizing cladribine with cyclodextrin. The Schultz et al. patent primarily addresses the problems inherent in previously described aqueous formulations of cladribine, particularly for subcutaneous and intramuscular injection. Schultz et al. have found that cladribine is not only significantly more soluble in aqueous media when formulated with cyclodextrin, but also is more stable against acid-catalyzed hydrolysis when combined with cyclodextrin. The latter finding is taught to be of particular benefit in the formulation of solid oral dosage forms, where the compound would normally undergo hydrolysis in the acid pH of the stomach contents. Schultz et al. do not appear to have described any actual work in connection with solid oral dosage forms. In fact, they describe only one method of preparing the solid dosage form, which is a melt extrusion process, in which the cladribine and cyclodextrin are mixed with other optional additives and then heated until melting occurs. Furthermore, the broad dosage ranges of 1 mg to 15 mg of cladribine and 100 mg to 500 mg of cyclodextrin listed in the patent suggest no criticality to the particular amount of cyclodextrin to be present with a given amount of cladribine in a solid oral dosage form. Indeed, these dosage ranges include many combinations which may be suitable as mixtures but not for complex formation. For example, a ratio of 1 mg of cladribine to 500 mg of cyclodextrin contains too much cyclodextrin, so that the drug would not readily leave the complex and achieve its therapeutic function. On the other hand, 15 mg of cladribine and only 100 mg of cyclodextrin would not be enough to complex that amount of cladribine.

The Schultz et al. patent does suggest improving the stability of cladribine in oral dosage forms by combining/complexing it with cyclodextrin, but does not suggest improving the drug's oral bioavailability by such means; in fact, the patent does not describe or suggest a method for enhancing or maximizing the bioavailability of cladribine from a solid oral dosage form of cladribine and cyclodextrin, or a composition specially designed to do so.

Many workers have studied the solubility of specific drugs in water containing various concentrations of selected cyclodextrins in order to demonstrate that increasing concentrations of cyclodextrins increase the solubility of the drugs at selected temperatures and pH levels, as for example reported in the Schultz et al. patent. Phase solubility studies have also been performed by various workers in order to elucidate the nature of the complex formation, for example, whether the cyclodextrin and drug form a 1:1 complex or a 1:2 complex; see, for example, Harada et al. U.S. Pat. No. 4,497,803, relating to inclusion complexes of lankacidin-group antibiotics with cyclodextrin, and Shinoda et al. U.S. Pat. No. 4,478,995, relating to a complex of an acid addition salt of (2'-benzyloxycarbonyl)phenyl trans-4-guanidinomethylcyclohexanecarboxylate with a cyclodextrin.

While Schultz et al. teach that a cladribine-cyclodextrin complex improves the water solubility and acid stability of cladribine, the art does not suggest how to maximize or enhance the benefits of the complexation in terms of bioavailability and interpatient variation when the complex is to be administered in a solid oral dosage form.

SUMMARY OF THE INVENTION

It has now been found that amorphous cyclodextrins can be combined with cladribine to form a particularly advantageous product which can be incorporated into a solid oral dosage form. This product is a complex cladribine-cyclodextrin complex, and the solid oral dosage form containing it improves oral bioavailability and/or achieves lower interpatient and/or intrapatient variation of the drug.

The present invention provides a complex cladribine-cyclodextrin complex which is an intimate amorphous admixture of (a) an amorphous inclusion complex of cladribine with an amorphous cyclodextrin and (b) amorphous free cladribine associated with amorphous cyclodextrin as a non-inclusion complex, and a pharmaceutical composition comprising said complex, formulated into a solid oral dosage form. Thus, the cyclodextrin itself is amorphous, the inclusion complex with cladribine is amorphous (and is preferably saturated with cladribine) and the free cladribine which forms the non-inclusion complex is amorphous.

The invention also provides a method for increasing or enhancing the oral bioavailability of cladribine comprising orally administering to a subject in need thereof, a pharmaceutical composition comprising a complex cladribine-cyclodextrin complex which is an intimate amorphous admixture of (a) an amorphous inclusion complex of cladribine with an amorphous cyclodextrin and (b) amorphous free cladribine associated with amorphous cyclodextrin as a non-inclusion complex, formulated into a solid oral dosage form which maximizes the amount of cladribine in the inclusion and non-inclusion complexes.

The invention further provides for treatment of conditions responsive to administration of cladribine in mammals by administering thereto the composition of the invention. Use of cladribine in the preparation of the pharmaceutical compositions of the invention for administration to treat cladribine-responsive conditions and for enhancing the oral bioavailability of cladribine is also provided.

Still further, the invention provides a process for the preparation of a complex cladribine-cyclodextrin complex which comprises the steps of:

(i) combining cladribine and an amorphous cyclodextrin in water at a temperature of from about 40 to about 80° C. and maintaining said temperature for a period of from about 6 to about 24 hours;

(ii) cooling the resultant aqueous solution to room temperature; and (iii) lyophilizing the cooled solution to afford an amorphous product.

In yet a further aspect the invention provides a pharmaceutical composition obtainable by a process comprising the steps of:

(i) combining cladribine and an amorphous cyclodextrin in water at a temperature of from about 40 to about 80° C. and maintaining said temperature for a period of from about 6 to about 24 hours;

(ii) cooling the resultant aqueous solution to room temperature;

(iii) lyophilizing the cooled solution to afford an amorphous product; and (iv) formulating the amorphous product into a solid oral dosage form.

BRIEF DESCRIPTION OF THE DRAWING

A more complete appreciation of the invention and its many attendant advantages will be readily understood by reference to the following detailed description and the accompanying drawing, wherein the sole FIGURE is a graphical representation of the results of a phase solubility study where various molar concentrations of hydroxypropyl-β-cyclodextrin (HPβCD) are plotted against various cladribine molar concentrations, with (●) representing the data points obtained for complexation under conditions specified in EXAMPLE 2 below.

DETAILED DESCRIPTION OF THE INVENTION

Throughout the instant specification and claims, the following definitions and general statements are applicable.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

The term "inclusion complex" as used herein refers to a complex of cladribine with the selected cyclodextrin wherein the hydrophobic portion of the cladribine molecule (the nitrogen-containing ring system) is inserted into the hydrophobic cavity of the cyclodextrin molecule. This is often referred to simply as a cyclodextrin complex of the drug.

The term "non-inclusion complex" refers to a complex which is not an inclusion complex; rather than the hydrophobic portion of cladribine being inserted in the cyclodextrin cavity, the non-inclusion complex is formed primarily by hydrogen-bonding of the hydroxyls and amino group on "free" cladribine, (i.e. cladribine not in the inclusion complex) to the hydroxyls on the exterior of the cyclodextrin torus (e.g. in the case of hydroxypropyl-β-cyclodextrin, hydroxypropyl and hydroxyl groups on the glucose rings). This is a more loosely-held association than an inclusion complex.

As used herein, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a composition, the term "comprising" means that the composition includes at least the recited features or components, but may also include additional features or components.

The terms "consists essentially of" or "consisting essentially of" have a partially closed meaning, that is, they do not permit inclusion of steps or features or components which would substantially change the essential characteristics of a process or composition; for example, steps or features or components which would significantly interfere with the desired properties of the compositions described herein, i.e., the process or composition is limited to the specified steps or materials and those which do not materially affect the basic and novel characteristics of the invention. The basic and novel features herein are the provision of a complex cladribine-cyclodextrin complex which is an intimate amorphous admixture of (a) an amorphous inclusion complex of cladribine with an amorphous cyclodextrin and (b) amorphous free cladribine associated with amorphous cyclodextrin as a non-inclusion complex, formulated into a solid oral dosage form, so as to provide improved bioavailability and/or lower interpatient and/or intrapatient variation following administration. Essential to the invention is the combination of the amorphous nature of the starting cyclodextrin, and the level of water solubility exhibited by cladribine (about 5 mg/ml at room temperature), and consequently its capability for hydrogen bonding, which can be taken advantage of under particular conditions described hereinafter, and which afford a special amorphous mixture uniquely well-suited for optimizing the oral bioavailability of cladribine.

The terms "consists of" and "consists" are closed terminology and allow only for the inclusion of the recited steps or features or components.

As used herein, the singular forms "a," "an" and "the" specifically also encompass the plural forms of the terms to which they refer, unless the content clearly dictates otherwise.

The term "about" is used herein to means approximately, in the region of, roughly, or around. When the term "about" is used in conjunction with a numerical range, it modifies that range by extending the boundaries above and below the numerical values set forth. In general, the term "about" or "approximately" is used herein to modify a numerical value above and below the stated value by a variance of 20%.

The term "amorphous" is used herein to refer to a noncrystalline solid. The cyclodextrins encompassed herein themselves are amorphous because they are each composed of a multitude of individual isomers, and their complexes with cladribine are also amorphous. Further, conditions for complexation can be selected (elevated temperature and prolonged complexation times, as described hereinafter) so that a supersaturated cladribine solution will be formed. When cooled, because of the amorphous nature of the complex and the cyclodextrin, some excess free cladribine does not precipitate but rather is trapped in amorphous form in intimate admixture with the (preferably saturated) amorphous cladribine-cyclodextrin inclusion complex. This excess cladribine forms a loosely-held association, or non-inclusion complex, with the cyclodextrin through hydrogen bonding. This, then, further increases the amount of cladribine in the product; this additional cladribine, because it is amorphous and also because it is in intimate admixture with the amorphous inclusion complex, is expected to be somewhat protected from degradation by stomach acid (although it may not be as protected as the cladribine which is in the form of the inclusion complex).

The term "saturated" when used in conjunction with a complex of cladribine in amorphous cyclodextrin means that the complex is saturated with cladribine, that is, the complex contains the maximum amount of cladribine which can be complexed (by means of both inclusion and non-inclusion complexes) with a given amount of cyclodextrin under the conditions of complexation used. A phase solubility study can be used to provide this information, as described in more detail hereinafter. (Conditions for the complexation are also described in more detail below.) Alternatively, a saturated complex may be arrived at empirically by simply adding cladribine to an aqueous solution of the selected cyclodextrin until no more cladribine goes into solution; ultimately, excess cladribine, if any, is removed (by filtration or centrifugation) and the solution lyophilized to provide the dry saturated complex.

The expression "substantially", as in "substantially free" means within 20% of the exact calculated amount, preferably within 10%, most preferably within 5%.

The term "interpatient variability" refers to variation among patients to which a drug is administered. The term "intrapatient variability" refers to variation experienced by a single patient when dosed at different times.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

In the specification and claims, the singular forms include plural referents unless the context clearly dictates otherwise. As used herein, unless specifically indicated otherwise, the word "or" is used in the "inclusive" sense of "and/or" and not the "exclusive" sense of "either/or."

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001).

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provided a thorough understanding of the present invention. The present invention may be practiced without some or all of these specific details. In other instances, well-known process operations have not been described in detail, in order not to unnecessarily obscure the present invention.

There is provided by the present invention compositions, as well as methods of making and of using pharmaceutical compositions, useful to achieve desirable pharmacokinetic properties. Such compositions stem from the discovery that solutions of cyclodextrin and cladribine in which cladribine is in a high thermodynamic state, when presented to the gastric mucosa through which they are absorbed are associated with improved cladribine absorption, as reflected by higher bioavailability and/or lower interpatient variation.

It is postulated, without wishing to so limit the invention, that upon dissolution (e.g., by contact with a fluid, such as a bodily fluid), dry compositions according to the invention form a locally saturated cladribine solution in which cladribine is in the state of highest thermodynamic activity (HTA), thus favoring absorption. Cladribine has a fairly low, although not insignificant, intrinsic aqueous solubility; it is in fact somewhat water soluble. The free cladribine formed from dissociation of the inclusion and non-inclusion complexes in a saturated aqueous solution seeks a more stable activity level by being absorbed through the gastric mucosa.

In view of the foregoing, it is apparent that to produce optimal pharmaceutical compositions, in a solid oral dosage form, these dosage forms should be formulated to release a localized saturated cladribine solution, upon contact of the solid dosage forms with body fluid at the mucosa, in which cladribine is in its HTA state. To provide such a localized saturated solution in vivo, it is important to first identify the optimal ratio of cladribine to amorphous cyclodextrin, which ratio is referred to herein as the HTA ratio, to be used in the solid dosage form.

The HTA ratio is empirically determined and is identified as the ratio of cladribine to amorphous cyclodextrin which corresponds to the maximum amount of cladribine that can be complexed with a given amount of the cyclodextrin. The HTA ratio may be determined using an empirical method such as a phase solubility study to determine the saturation concentration of cladribine that can be solubilized with different concentrations of amorphous cyclodextrin solutions. Hence, the method identifies the concentrations at which a saturated cladribine-cyclodextrin complex is formed. It is noted that the molar ratio represented by a point on the phase solubility graph shows how many moles of amorphous cyclodextrin are the minimum needed to maintain the drug in the complex, under given conditions; this may then be converted to a weight ratio. For example, if a phase solubility diagram shows that 9 moles of a given cyclodextrin are needed to maintain the cladribine in a saturated complex, then multiplying the number of moles of cladribine by its molecular weight and multiplying the number of moles of the selected cyclodextrin by its molecular weight, one can arrive at the ratio of the products as an appropriate optimized weight ratio. A phase solubility study also provides information about the nature of the cladribine-cyclodextrin inclusion complex formed, for example whether the inclusion complex is a 1:1 complex (1 molecule of drug complexed with 1 molecule of cyclodextrin) or a 1:2 complex (1 molecule of drug complexed with 2 molecules of cyclodextrin).

In accordance with the present invention, one can start using either the selected amorphous cyclodextrin, such as hydroxypropyl-β-cyclodextrin (HPβCD) or hydroxypropyl-γ-cyclodextrin, or cladribine as the fixed variable to which an excess of the other is added to identify various solubility data points (indicating saturated cladribine-cyclodextrin complexes) and draw the resultant line. Typically, cladribine is added to an aqueous solution having a known concentration of amorphous cyclextrin under conditions empirically found to promote complex formation. Generally, the complexation is conducted with heating, for example at about 45 to about 60° C. for a significant period of time, e.g., at least 6-9 hours; it is believed that even better results can be obtained by heating at up to about 80° C. for up to 24 hours. Excess precipitated cladribine is then removed and the cladribine concentration is subsequently measured. This concentration represents the amount of cladribine solubilized for a given amorphous cyclodextrin concentration. This process is repeated for a different known concentration of cyclodextrin until several data points are obtained. Each data point represents the concentration of the cladribine dissolved in a known concentration of the selected amorphous cyclodextrin. The data points are then plotted to show the concentration of cladribine against the various cyclodextrin concentrations used. The graph is a phase solubility diagram which can be used to determine the amount of cladribine for any specific concentration of cyclodextrin used to form the solution under a given set of complexation conditions. It will be appreciated that the aqueous solubility of cladribine is about 5 mg/ml at room temperature and would be higher at elevated temperature. Consequently, the data points correspond to the amount of cladribine dissolved in aqueous HPβCD or other amorphous cyclodextrin under the selected conditions; when later lyophilized, the solution yields a complex cladribine-cyclodextrin complex which is an intimate amorphous admixture of (a) an amorphous inclusion complex of cladribine with an amorphous cyclodextrin and (b) amorphous free cladribine associated with amorphous cyclodextrin as a non-inclusion complex. If equilibrium conditions are reached during the complexation, the amorphous cladribine-cyclodextrin complex will be saturated with cladribine.

One of skill in the art will appreciate that concentrations at which saturated complexes of cladribine with amorphous cyclodextrins are formed (and thus HTA ratios as well) may be identified by a variety of alternative methodologies. Accordingly, any method known in the field suitable to identify these concentrations is within the scope of the invention.

It has been discovered that desirable pharmacological properties (improved bioavailability and/or coefficient of variation as compared to traditional approaches) are associated with mixtures of inclusion complexes and non-inclusion complexes of cladribine and cyclodextrin.

Using intrinsically amorphous cyclodextrins, for example hydroxypropyl-β-cyclodextrin, hydroxypropyl-γ-cyclodextrin, randomly methylated cyclodextrins, and the like, with cladribine, which is a somewhat water soluble compound (capable of H-bonding through its free hydroxyl and amino groups), the cladribine provides increased solubility in solutions of these cyclodextrins. Not only is there increased water solubility but also H-bonded association of the cladribine with the cyclodextrin, separately from the actual inclusion complexed material.

One of skill in the art will appreciate that the phase solubility diagram for each given starting concentration ratio represents the starting point of one's investigation on the basis of which variables (reactants' concentrations, temperature and time) may be altered to promote inclusion complex and non-inclusion complex associations favoring a higher or lower proportion of either type of association in the final product. Departure from the ratio of cladribine to cyclodextrin, the temperature and/or the dilution empirically found to promote equilibrium towards complex formation is then analyzed to promote the formation of mixtures of inclusion complexes and non-inclusion complexes of cladribine and cyclodextrin in various proportions according to the invention.

Thus, for example, by starting with more diluted cyclodextrin (i.e., larger water volumes than that used for solubility plot analysis) logically will accommodate more cladribine in solution sequestering more of the same from complex formation. Upon evaporation, some of the solubilized cladribine will tend to associate with cyclodextrin in a non-inclusion complex fashion. By altering the initial dilution, one may shift equilibrium towards inclusion complex or non-inclusion complex formation. Similarly, by increasing complexation temperature, the water solubility of cladribine may be increased while decreasing the stability of inclusion complexes, thus promoting non-inclusion complexes. Thus, by altering complexation temperature, one may shift equilibrium towards inclusion complex or non-inclusion complex formation. Finally, complexation time may be altered to favor the formation of mixtures of inclusion complexes and non-inclusion complexes of cladribine and cyclodextrin according to the invention.

As exemplified hereinafter, it is possible to maximize the cladribine in solid amorphous mixtures, by forcing additional cladribine into solution (using more dilute solutions of cyclodextrin, higher temperatures and longer complexation times, as indicated above). When the solution is cooled off, the extensively amorphous nature of these cyclodextrins does not allow crystallization of an excess amount of cladribine beyond that which forms an inclusion complex with the cyclodextrin; and upon freeze-drying/lyophilization, one obtains an amorphous mixture of cladribine-cyclodextrin inclusion complex (which is amorphous) and amorphous free cladribine, loosely associated with uncomplexed cyclodextrin (and even with complexed cyclodextrin) by hydrogen-bonding, that is, the non-inclusion complex.

As shown in the EXAMPLES, this may be done by maximizing solubilization by elevating the temperature (for example, to about 50° to 80° C.), and stirring for many hours (up to 24 hours) before freeze-drying. The weight/weight ratios obtained were about 1:14 and 1:11. The apparent optimum weight/weight ratio under these exemplified conditions is the higher of these, or about 1:14 of cladribine:cyclodextrin. If too much excess cladribine is added to the complexation medium, then crystallization of some of the cladribine takes place, which would in turn result in some crystalline cladribine in the product; this undesired excess cladribine is not in solution and is not H-bonded to the amorphous cyclodextrin and lowers the weight ratio. Therefore, it is desirable to carefully control the amount of excess cladribine beyond that which will form the inclusion complex to only the amount which will dissolve in the solution. The desired amorphous mixture of amorphous inclusion complex and amorphous free cladribine can be termed a "complex cladribine-cyclodextrin complex," which includes both inclusion and non-inclusion/H-bonded complexes. The inclusion complex is a complex of cladribine inserted into the hydrophobic cavity of the selected amorphous cyclodextrin, while the non-inclusion/H-bonded complex is amorphous free cladribine loosely hydrogen-bonded to the cyclodextrin. It is estimated that about two-thirds (60 to 70%) of the cladribine will be in the non-inclusion complex, with the remaining one third (30 to 40%) being in the inclusion complex when the product is obtained as exemplified hereinbelow (17% HPβCD solution, 45 to 50° C. complexation temperature for about 9 hours); by increasing the percentage of cyclodextrin used and/or manipulating the temperature, products can be readily obtained in which a much greater proportion of the amorphous mixture is in the form of the inclusion complex. In the case of a representative amorphous cyclodextrin, hydroxypropyl-β-cyclodextrin (HPβCD) a cladribine:cyclodextrin weight ratio of from about 1:10 to about 1:16 is appropriate for the exemplified conditions; the ratio is expected to be the same for hydroxypropyl-γ-cyclodextrin under those conditions. The material obtained is characterized by rapid dissolution of the cladribine in aqueous media.

Freeze-drying, also known as lyophilization, comprises three basic stages: first a freezing stage, then a primary drying stage and finally a secondary drying stage. EXAMPLE 2 below provides details of lyophilization as conducted on the batches described therein. This procedure can be further optimized by following the principles described by Xiaolin (Charlie) Tang and Michael J. Pikal in *Pharmaceutical Research*, Vol. 21, No. 2, February 2004, 191-200, incorporated by reference herein in its entirety and relied upon.

The above-described method requires amorphous cyclodextrins rather than originally crystalline cyclodextrins which have relatively low water solubilities, such as α-, β- or γ-cyclodextrin, 2,6-dimethyl-β-cyclodextrin and the like, because these cyclodextrins would allow crystallization of cladribine in excess of that forming an inclusion complex and therefore would not afford the desired amorphous mixture. The method also would not be useful if cladribine were highly hydrophobic/lipophilic, because in such a situation the drug would not have intrinsic aqueous solubility/H-bonding capability and could not provide the unique mixture obtained herein. However, in point of fact, cladribine has an aqueous solubility of 5 mg/ml at room temperature, thus a significant amount of the drug will be simply soluble in the water phase especially at higher than room temperature; also, as in the case of HPβCD, for example, some of the cladribine will be associated by hydrogen-bonding to the 2-hydroxypropyl and free glucose-OH groups in the cyclodextrin via the two hydroxy functions found in the deoxyadenosine moiety of the cladribine.

The cyclodextrins within the scope of this invention are amorphous derivatives of the natural cyclodextrins α-, β- or γ-cyclodextrin wherein one or more of the hydroxy groups are substituted, for example, by alkyl, hydroxyalkyl, carboxyalkyl, alkylcarbonyl, carboxyalkoxyalkyl, alkylcarbonyloxyalkyl, alkoxycarbonylalkyl or hydroxy-(mono or polyalkoxy) alkyl groups; and wherein each alkyl or alkylene moiety preferably contains up to six carbons. Although commonly referred to as a single entity, an amorphous cyclodextrin is actually a mixture of many different entities, since the substitutent groups can be located on various hydroxyls of the basic cyclodextrin structure. This in turn results in the amorphous nature of these cyclodextrins, which is indeed well-known. Moreover, these cyclodextrins can be obtained in varying degrees of substitution, for example from 1 to 14, preferably from 4 to 7; the degree of substitution is the approximate average number of substitutent groups on the cyclodextrin molecule, for example, the approximate number of hydroxypropyl groups in the case of the hydroxypropyl-β-cyclodextrin molecule, and all such variations are within the ambit of this invention. Substituted amorphous cyclodextrins which can be used in the invention include polyethers, for example, as described in U.S. Pat. No. 3,459,731. Further examples of substituted cyclodextrins include ethers wherein the hydrogen of one or more cyclodextrin hydroxy groups is replaced by $C_{1-6}$-alkyl, hydroxy-$C_{1-6}$alkyl, carboxy-$C_{1-6}$ alkyl or $C_{1-6}$alkyloxycarbonyl-$C_{1-6}$alkyl groups or mixed ethers thereof. In particular, such substituted cyclodextrins are ethers wherein the hydrogen of one or more cyclodextrin hydroxy groups is replaced by $C_{1-3}$alkyl, hydroxy-$C_{2-4}$alkyl or carboxy-$C_{1-2}$alkyl or more particularly by methyl, ethyl, hydroxyethyl, hydroxypropyl, hydroxybutyl, carboxymethyl or carboxyethyl. The term "$C_{1-6}$alkyl" is meant to include straight and branched saturated hydrocarbon radicals, having from 1 to 6 carbon atoms such as methyl, ethyl, 1-methylethyl, 1,1-dimethylethyl, propyl, 2-methylpropyl, butyl, pentyl, hexyl and the like. Other cyclodextrins contemplated for use herein included glucosyl-β-cyclodextrin and maltosyl-β-cyclodextrin. Of particular utility in the present invention are randomly methylated β-cyclodextrin and polyethers such as hydroxypropyl-β-cyclodextrin, hydroxyethyl-β-cyclodextrin, hydroxypropyl-γ-cyclodextrin, and hydroxyethyl-γ-cyclodextrin, as well as sulfobutyl ethers, especially β-cyclodextrin sulfobutyl ether. In addition to simple cyclodextrins, branched cyclodextrins and cyclodextrin polymers may also be used. Other cyclodextrins are described, for example, in *Chemical and Pharmaceutical Bulletin* 28: 1552-1558 (1980); Yakugyo Jiho No. 6452 (28 Mar. 1983); *Angew. Chem. Int. Ed. Engl.* 19: 344-362 (1980); U.S. Pat. Nos. 3,459,731 and 4,535,152; European Patent Nos. EP 0 149 197A and EP 0 197 571A; PCT International Patent Publication No. WO90/12035; and UK Patent Publication GB 2,189, 245.

References describing cyclodextrins for use in the compositions according to the present invention, and/or which provide a guide for the preparation, purification and analysis of cyclodextrins include the following: *Cyclodextrin Technology* by Jozsef Szejtli, Kluwer Academic Publishers (1988) in the chapter Cyclodextrins in Pharmaceuticals; *Cyclodextrin Chemistry* by M. L. Bender et al., Springer-Verlag, Berlin (1978); *Advances in Carbohydrate Chemistry*, Vol. 12, Ed. By M. L. Wolfrom, Academic Press, New York in the chapter "The Schardinger Dextrins" by Dexter French, pp. 189-260; *Cyclodextrins and their Inclusion Complexes* by J. Szejtli, Adakemiai Kiado, Budapest, Hungary (1982); I. Tabushi, *Acc. Chem. Research*, 1982, 15, pp. 66-72; W. Sanger, *Angewandte Chemie*, 92, p. 343-361 (1981); A. P. Croft et al., *Tetrahedron*, 39, pp. 1417-1474 (1983); Irie et al. *Pharmaceutical Research*, 5, pp. 713-716 (1988); Pitha et al., *Int. J. Pharm.* 29, 73 (1986); U.S. Pat. Nos. 4,659,696 and 4,383, 992; German Patent Nos. DE 3,118,218 and DE-3,317,064; and European Patent No. EP 0 094 157A. Patents describing hydroxyalkylated derivative of β- and γ-cyclodextrin include Pitha U.S. Pat. Nos. 4,596,795 and 4,727,064, Müller U.S. Pat. Nos. 4,764,604 and 4,870,060 and Müller et al. U.S. Pat. No. 6,407,079.

Amorphous cyclodextrins of particular interest for complexation with cladribine include: hydroxyalkyl, e.g. hydroxyethyl or hydroxypropyl, derivatives of β- and γ-cyclodextrin; carboxyalkyl, e.g. carboxymethyl or carboxyethyl, derivatives of β- or γ-cyclodextrin; β-cyclodextrin sulfobutyl ether; and randomly methylated β-cyclodextrin. 2-Hydroxypropyl-β-cyclodextrin (HPβCD), 2-hydroxypropyl-γ-cyclodextrin (HPγCD), randomly methylated β-cyclodextrin, β-cyclodextrin sulfobutyl ether, carboxymethyl-β-cyclodextrin (CMβCD) and carboxymethyl-γ-cyclodextrin (CMγCD) are of special interest, especially hydroxypropyl-β-cyclodextrin and hydroxypropyl-γ-cyclodextrin.

Compositions of an amorphous mixture of amorphous free cladribine and an amorphous, preferably saturated, cladribine-cyclodextrin inclusion complex for use in the present invention can be prepared under conditions favoring complex formation in a liquid environment as described and as exemplified herein. The resultant liquid preparations can be subsequently converted to a dry form suitable for administration as a solid oral or transmucosal dosage form.

One of skill will appreciate that a variety of approaches are available in the field to prepare compositions as described herein. One available method exemplified herein includes the steps of mixing the cladribine in an aqueous solution of an amorphous cyclodextrin, separating un-dissolved cladribine (e.g., by filtering or centrifugation), and lyophilizing or freeze-drying the saturated solution to form a solid amorphous mixture.

Pharmaceutical compositions according to the invention may optionally include one or more excipients or other pharmaceutically inert components. One of the advantages of the invention, however, is that cladribine drug forms as described herein can be prepared with the minimal amount of excipients necessary for shaping and producing the particular form, such as a tablet or patch. Excipients may be chosen from those that do not interfere with cladribine, with cyclodextrin or with complex formation.

Dosage forms are optionally formulated in a pharmaceutically acceptable vehicle with any of the well-known pharmaceutically acceptable carriers, diluents, binders, lubricants, disintegrants, scavengers, flavoring agents, coloring agents, and excipients (see *Handbook of Pharmaceutical Excipients*, Marcel Dekker Inc., New York and Basel (1998); Lachman et al. Eds., *The Theory and Practice of Industrial Pharmacy*, 3$^{rd}$ Ed., (1986); Lieberman et al., Eds. *Pharmaceutical Dosage Forms*, Marcel Dekker Inc., New York and Basel (1989); and *The Handbook of Pharmaceutical Excipients*, 3$^{rd}$ Ed., American Pharmaceutical Association and Pharmaceutical Press, 2000); see also *Remington's Pharmaceutical Sciences*, 18$^{th}$ Ed., Gennaro, Mack Publishing Co., Easton, Pa. (1990) and *Remington: The Science and Practice of Pharmacy*, Lippincott, Williams & Wilkins, (1995)). A simple solid oral dosage form consists of the amorphous mixture of amorphous free cladribine and amorphous cladribine-cyclodextrin complex (preferably saturated) as described above, i.e. the complex cladribine-cyclodextrin complex, compressed with a small amount (e.g. about 1% by weight) of a suitable binder or lubricant such as magnesium stearate.

In certain instances, oral absorption may be further facilitated by the addition of various excipients and additives to increase solubility or to enhance penetration, such as by the modification of the microenvironment.

The methods and pharmaceutical compositions described herein offer novel therapeutic modalities for the treatment of patients in need of treatment with cladribine. As shown herein, the invention addresses the problems of poor bioavailability traditionally associated with oral cladribine.

The compositions of the invention are particularly suitable as modalities for the treatment of any cladribine-responsive disease. Several disease states responsive to cladribine are well-documented in the literature (see infra). For any target disease state, an effective amount of the complex cladribine-cyclodextrin complex, i.e. the amorphous mixture of the optimized amorphous saturated cladribine-amorphous cyclodextrin complex with amorphous free cladribine as described above is used (e.g., an amount effective for the treatment of multiple sclerosis, rheumatoid arthritis, or leukemia).

The term "therapeutically effective amount" or "effective amount" is used to denote treatments at dosages effective to achieve the therapeutic result sought. Therapeutically effective dosages described in the literature include those for hairy cell leukemia (0.09 mg/kg/day for 7 days), for multiple sclerosis (from about 0.04 to about 1.0 mg/kg/day (see U.S. Pat. No. 5,506,214)); for other diseases, see also U.S. Pat. Nos. 5,106,837 (autohemolytic anemia); 5,310,732 (inflammatory bowel disease); 5,401,724 (rheumatoid arthritis); 5,424,296 (malignant astrocytoma); 5,510,336 (histiocytosis); 5,401, 724 (chronic myelogenous leukemia); and 6,239,118 (atherosclerosis).

Further, various dosage amounts and dosing regimens have been reported in the literature for use in the treatment of multiple sclerosis; see, for example: Romine et al., *Proceed-* ings of the Association of American Physicians, Vol. 111, No. 1, 35-44 (1999); Selby et al., *The Canadian Journal of Neurological Sciences,* 25, 295-299 (1998); Tortorella et al., *Current Opinion in Investigational Drugs,* 2 (12), 1751-1756 (2001); Rice et al., *Neurology,* 54, 1145-1155 (2000); and Karlsson et al., *British Journal of Haematology,* 116, 538-548 (2002); all of which are incorporated by reference herein in their entireties and relied upon.

Moreover, the route of administration for which the therapeutically effective dosages are taught in the literature should be taken into consideration. While the instant compositions optimize the bioavailability of cladribine following oral administration, it will be appreciated that even optimal bioavailability from oral dosage forms is not expected to approach bioavailability obtained after intravenous administration, particularly at early time points. Thus, it is often appropriate to increase a dosage suggested for intravenous administration to arrive at a suitable dosage for incorporation into a solid oral dosage form. At the present time, it is envisioned that, for the treatment of multiple sclerosis, 10 mg of cladribine in the instant complex cladribine-cyclodextrin complex in the instant solid dosage form would be administered once per day for a period of five to seven days in the first month, repeated for another period of five to seven days in the second month, followed by ten months of no treatment. Alternatively the patient would be treated with 10 mg of cladribine in the instant complex cladribine-cyclodextrin complex in the instant dosage form once per day for a period of five to seven days per month for a total of six months, followed by eighteen months of no treatment.

Furthermore, one of skill will appreciate that the therapeutically effective amount of cladribine administered herein may be lowered or increased by fine tuning and/or by administering cladribine according to the invention with another active ingredient. The invention therefore provides a method to tailor the administration/treatment to the particular exigencies specific to a given mammal. Therapeutically effective amounts may be easily determined, for example, empirically by starting at relatively low amounts and by step-wise increments with concurrent evaluation of beneficial effect.

As noted in the preceding paragraph, administration of cladribine in accord with this invention may be accompanied by administration of one or more additional active ingredients for treating the cladribine-responsive condition. The additional active ingredient will be administered by a route of administration and in dosing amounts and frequencies appropriate for each additional active ingredient and the condition being treated. For example, in the treatment of multiple sclerosis, other useful drugs include interferon beta (Rebif®, Betaseron®/Betaferon®, Avonex®), identical to the naturally occurring protein found in the human body; glatiramer acetate (Copaxone®), a random chain (polymer) of the amino acids glutamic acid, lysine, alanine and tyrosine; natalizumab (Antegren®), a monoclonal antibody; alemtuzumab (Campath-1H®), a humanized anti-CD52 monoclonal antibody; 4-aminopyridine (also known as 4-AP and Fampridine), a drug that blocks the potassium channels in neurons; and amantadine, an anti-viral agent which improves muscle control and reduces muscle stiffness and is used to alleviate the symptoms of fatigue in multiple sclerosis, a purpose for which pemoline (Cylert®) and L-Carnitine (a herbal product) may also be useful. In the treatment of hairy cell leukemia, additional active ingredients may include interferon alpha, pentostatin, fludarabine, rituximab (an anti-CD 20 monoclonal antibody) and the anti-CD22 recombinant immunotoxin BL 22; other additional active ingredients may be appropriate in other types of leukemias. In the treatment of rheumatoid arthritis, there are many other active ingredients which may be selected. These include NSAIDS (non-steroidal anti-inflammatory drugs), which are of three types: salicylates such as aspirin, traditional NSAIDS such as ibuprofen and indomethacin, and COX-2 inhibitors such as celecoxib (Celebrex®), rofecoxib (Vioxx®), meloxicam (Mobic®), valdecoxib (Bextra®), lumiracoxib (Prexige®) and etoricoxib (Arcoxia®). Other drugs useful in treating rheumatoid arthritis which may be used in conjunction with the present invention include DMARDS, glucocorticoids, biological response modifiers and non-NSAID analgesics. DMARDS are disease-modifying anti-rheumatic drugs which include methotrexate, plaquenil, leflunomide (Arava®), sulfasalazine, gold, penicillamide, cyclosporine, methyl cyclophosamide and azathioprine. Glucocorticoids include dexamethasone, prednisolone, triamcinolone and many others. Biological response modifiers (which restore the disease-fighting ability of the immune system), include etanercept (Enrel®), a tumor-necrosis factor inhibitor, infliximab (Remicade®), which is also an anti-TNF drug, anakinra (Kineret®), a selective IL-1 blocker, and Humira®, a human monoclonal antibody which is another anti-TNF drug. The non-NSAID analgesics include acetaminophen as well as narcotic analgesics such as hydrocodone, oxycodone and propoxyphene. Generally speaking, those drugs which work by a mechanism different from that of cladribine are particularly useful for concomitant therapy with the cladribine composition described herein. Those drugs which are effective by the oral route of administration and which are compatible with the instant cladribine complexes in a single dosage form may be incorporated into the instant dosage forms; otherwise, they should of course be separately administered in amounts, frequencies and via administration routes suitable to them.

As used herein, "treating" means reducing, preventing, hindering the development of, controlling, alleviating and/or reversing the symptoms in the individual to which a compound of the invention has been administered, as compared to the symptoms of an individual not being treated according to the invention. A practitioner will appreciate that the complexes, compositions, dosage forms and methods described herein are to be used in concomitance with continuous clinical evaluations by a skilled practitioner (physician or veterinarian) to determine subsequent therapy. Such evaluation will aid and inform in evaluating whether to increase, reduce or continue a particular treatment dose, and/or to alter the mode of administration.

The methods of the present invention are intended for use with any subject/patient that may experience the benefits of the methods of the invention. Thus, in accordance with the invention, the terms "subjects" as well as "patients" include humans as well as non-human subjects, particularly domesticated animals.

Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

EXAMPLES

Example 1

Phase Solubility Study

A phase solubility study can be carried out as follows. Excess cladribine is added to cyclodextrin solutions of various concentrations of hydroxypropyl-β-cyclodextrin (HPβCD) and allowed to complex as described in EXAMPLE 2 below. The excess, undissolved cladribine is removed by filtration. The amount of cladribine in the complexation solution is measured to obtain a data point. This process is repeated with different known concentrations of HPβCD until several data points are obtained. These data points are then plotted graphically, each data point representing the amount of cladribine that can be dissolved in water with a specific concentration of cyclodextrin. Points on the line generated by the data points represent ratios for the product. One of skill in the art will realize the same results will be generated if excess cyclodextrin is added to cladribine solutions of known concentration.

The molar concentrations of cladribine to cyclodextrin obtained are plotted and presented graphically. A representative phase solubility diagram is shown in the FIGURE. The plotted lines for cladribine-HPβCD represent cladribine solubilization for the conditions tested, that is, the ratio of the concentration of cladribine to the concentration of cyclodextrin. The area above each of the plotted lines represents conditions where excess insoluble cladribine is present. The area below each of the plotted lines represents the conditions where cyclodextrin is in excess.

The plot for cladribine-HPβCD shown in the FIGURE is approximately linear; this is indicative of a 1:1 complex, in which one molecule of the drug is complexed with one molecule of cyclodextrin. The FIGURE also shows that additional cyclodextrin is needed to maintain the cladribine in the complex. For example, about 0.14 mole of HPβCD is needed to maintain about 0.049 mole of cladribine dissolved under the selected conditions, which will ultimately provide the amorphous mixture of the amorphous, preferably saturated, cladribine-HPβCD inclusion complex and amorphous free cladribine (as a non-inclusion complex). Under the conditions of EXAMPLE 2 below, a significant portion of the cladribine in the product can be expected to be not in the inclusion complex but rather in amorphous form loosely held in intimate admixture therewith by hydrogen bonding as a non-inclusion complex.

Example 2

Preparation of Cladribine-Cyclodextrin Complex for Human Trials

Cladribine is complexed with HPβCD by the following method.

In 825 mL of distilled water, 172.5 g of hydroxypropyl-β-cyclodextrin are dissolved (forming an approximately 17% solution), then cladribine is added and the mixture is stirred at about 45 to about 50° C. for about nine hours. Stirring is continued for an additional 6 to 9 hours at room temperature. Any undissolved cladribine is removed by filtration and the solution is cooled to room temperature. To form the amorphous mixture of amorphous cladribine-cyclodextrin complex and amorphous free cladribine, the aqueous cladribine-cyclodextrin solution is dried by lyophilization prior to incorporation into solid oral tablets. The lyophilization procedure comprises a freezing stage of rapidly bringing the complexation solution to about −40° C. to about −80° C. (e.g., about −45° C.) for approximately 2 to 4 hours (preferably about 3 to 4 hours), followed by a primary drying stage at about −25° C. for approximately 80-90 hours, typically under low pressure, and a second drying stage at about 30° C. for about 15-20 hours.

Product made by the foregoing general procedure can be analyzed by HPLC (utilizing a Hypersil ODS 3 micron column and an acetonitrile based mobile phase, with UV detection at 264 nm) to find the weight ratio of cladribine to cyclodextrin in the final product. Final product preparations can be further characterized by methods known in the art, including, for example by inspecting appearance, ascertaining the overall impurity content by HPLC, ascertaining the water content using a Karl Fischer titrator, determining the dissolution profile by a standard method, for example using USP<711>Apparatus II equipment and UV detection at 264 nm, inspecting the content uniformity and performing quantitative assay by HPLC analysis of the active ingredient.

Two batches of cladribine/cyclodextrin product, FD04 and FD05, were made by the foregoing general procedure as follows:

Purified water (825 mL) was pre-heated at 48° C. (target range 45° C. to 50° C.) in a 1-liter glass vessel by immersion in a water bath. The heated water was stirred to achieve a controlled central vortex. 2-hydroxypropyl-β-cyclodextrin (172.50 g) was weighed and slowly added to the heated water over a period of 40 minutes. The resulting solution was stirred for a further 10 minutes to ensure complete dissolution of the cyclodextrin. Cladribine (12.00 g for FD04 and 18.75 g for FD05) was weighed and added to the stirred cyclodextrin solution, which turned cloudy before becoming clear. The resulting clear solution was maintained at 48° C. and continually stirred for 9 hours. Stirring continued for a further 7 hours while the solution cooled to room temperature.

Use of a larger amount of cladribine in the preparation of FD05 was part of an attempt to optimize the procedure; however, it was found that the initial amount of cladribine in that case was too great and precipitation was observed at the end of the cooling step for batch FD05. The solution was filtered to remove the precipitate. Analysis of the resultant product revealed (assay value=87.2%) that 16.35 g of cladribine had been incorporated into the cyclodextrin complex in the case of FD05. No filtration was required for batch FD04, indicating that the amounts used in the preparation of FD04 were more appropriate and that the FD05 procedure could be optimized by beginning with a smaller amount of cladribine (16.35 g rather than 18.75 g), thus avoiding the filtration step.

After cooling to room temperature and, in the case of FD05, filtering, the solutions were filled into 100 mL lyophilization vials (20 mL solutions per vial), the filled vials were partially stoppered and lyophilized. The lyophilization included freezing at −45° C. for about 200 minutes, a primary drying phase at −25° C. under a pressure of 100 mTorr for about 5,200 minutes and a secondary drying phase at 30° C. for about 1,080 minutes as set forth below:

TABLE I

| Step | Process | Temperature | Pressure (mTorr) | Time (min) |
|---|---|---|---|---|
| 1 | Load | 4° C. | | |
| 2 | Load Hold | 4° C. | n/a | 120 |
| 3 | Ramp | −45° C. | n/a | 120 |
| 4 | Freezing | −45° C. | n/a | 200 |
| 5 | Ramp | −25° C. | 100 | 120 |
| 6 | Primary drying | −25° C. | 100 | 5200 |
| 7 | Ramp | 30° C. | 50 | 240 |
| 8 | Secondary drying | 30° C. | 50 | 1080 |
| 9 | Finish | 30° C. | Vials closed under vacuum | |

The FD04 and FD05 batches of cladribine/cyclodextrin product made by the foregoing procedure were analyzed by HPLC (utilizing a Hypersil ODS 3 micron column and an acetonitrile based mobile phase with UV detection at 264 nm) and empirically found to have the following characteristics:

TABLE II

| Lot No. | Cladribine: HPβCD w/w | Cladribine: HPβCD Weight Ratio |
|---|---|---|
| FD04 | 12.00 g:172.50 g | 1:14.38 |
| FD05 | 16.35 g:172.50 g | 1:10.55 |

The products were analyzed by DSC thermograms and X-ray diffraction methods to determine any free crystalline cladribine in the lyophilized material. Importantly, the samples exhibited no transitions in the region of 210° C. to 230° C., which is associated with the melting of crystalline cladribine. In both cases, no significant thermal activity was recorded in the range of 210° C. to 230° C., suggesting that the complexes obtained at the end of the lyophilization do not have any significant amount of free crystalline cladribine, considering the sensitivity of the analytical method (up to 3% w/w). This conclusion was supported by the absence of peaks for crystalline cladribine from X-ray diffraction traces for both complexes FD04 and FD05.

The products are amorphous mixtures of amorphous cladribine-HPβCD inclusion complex and amorphous free cladribine hydrogen-bonded to the cyclodextrin as a non-inclusion complex. The cladribine:HPβCD weight ratios obtained were about 1:14 and 1:11.

Generally speaking, amorphous mixtures within the scope of the present invention have cladribine:HPβCD weight ratios of from about 1:10 to 1:16.

Example 3

Preparation of Oral Tablets

Tablets were manufactured using batches of amorphous mixtures FD04 and FD05 described in EXAMPLE 2 for use in a clinical study.

Batch N0120 was manufactured using cladribine-2-HP-βCD complex mixture DF05 to a batch size of 3,000 tablets and batch N0126 was manufactured using cladribine-HPβCD complex mixture FD04 to a batch size of 800 tablets. The master formulations for the two batches are shown in TABLE III. Batch N0120 represented 3.0 g tablets and Batch N0126 represented 10 mg tablets for clinical study.

TABLE III

| Constituent | Lot Number | mg/tablet 3.0 mg Batch N0120 | mg/tablet 10.0 mg Batch N0126 |
|---|---|---|---|
| Cladribine-HPβCD complex mix | FD05 | 30.60* | |
| Cladribine-HPβCD complex mix | FD04 | | 153.75** |
| Sorbitol powder NF | 1007403 | 68.4 | 44.25 |
| Magnesium stearate NF | 1006280 | 1.00 | 2.00 |
| Total | | 100.00 | 200.00 |

*Equivalent to 3.0 mg cladribine per tablet.
**Equivalent to 10.0 mg cladribine per tablet.

The following table sets forth the method of manufacture of the Batch N0120 and N0126 tablets.

TABLE IV

1. Pre-mix the magnesium stearate with an approximately equal quantity of sorbitol power.
2. Pass the cladribine-HPβCD complex and the remainder of the sorbitol powder into a one-liter glass jar via a 40-mesh screen.
3. Blend the contents for 10 minutes at 12 rpm.
4. Pass the magnesium stearate/sorbitol powder pre-mix into the glass jar via the 40-mesh screen.
5. Blend the final mixture for 5 minutes at 12 rpm.
6. Compress into 3.0 mg and 10.0 mg tablets at a target compression weight of 100 mg and 200 mg, respectively.

Both the Batch N0120 3.0 mg tablets and the Batch N0126 10.0 mg tablets were round, with one side flat-beveled edged and the other side shallow convex. The Batch N0120 3.0 mg tablets had an average weight of 100 mg, a thickness of 2.7 mm, a friability of 0.2%, a hardness of 4 Kp and a disintegration time of 3 minutes. The Batch N0126 10.0 mg tablets had an average weight of 198 mg, a thickness of 4.2 mm, a friability of 1%, a hardness of 2.8 Kp and a disintegration time of 5 minutes 42 seconds.

The Batch N0120 3.0 mg and N0126 10.0 mg tablets were used in the clinical study summarized in EXAMPLE 5 below.

Example 4

Clinical Study

Relative Bioavailability

The objective of this study was to assess the relative bioavailability of three oral cladribine formulations: (1) a cyclodextrin-based formulation according to the instant invention (Tablet 1: complex FD05, i.e. Batch No. N0120 tablets described above); (2) a mucoadhesive formulation (Tablet 2: containing 3.0 mg cladribine, 10 mg of Carbopol 71G NF, 22.2 mg of dicalcium phosphate, 64.3 mg of lactose and 0.5 mg of magnesium stearate, Batch No. N0121); and (3) a hard-gel capsule (Capsule containing 3.0 mg cladribine, 5.0 mg Carbopol 974P, 91.3 mg Avicel PH101, 100.0 mg Avicel PH102, 0.2 mg colloidal silicon dioxide and 0.5 mg magnesium stearate, Batch No. RD03030) in comparison with one fixed subcutaneous cladribine administration (reference formulation) in patients with MS (multiple sclerosis).

This study was a 2 center, open-label, randomized, 4-way crossover single dose study using twelve patients with MS. Patients received randomly three different fixed oral doses (3.0 mg) and a fixed subcutaneous dose of 3.0 mg. The four treatment days were separated by a drug-free interval of at least 5 days. In each treatment period, blood samples were collected over a 24-hour period for evaluation of plasma cladribine.

The plasma concentration of cladribine was measured by a HPLC/MS/MS method. Using this method, the relationship between concentration versus peak area ratio was found to be linear within the range of 100 pg/ml to 50,000 pg/ml for cladribine. The limit of quantification was 100 pg/ml. Analysis of samples was carried out in 16 runs. No calibrator had to be excluded from fitting of the calibration curve and accuracy of each quality control sample met the GLP requirements.

576 clinical plasma samples were analyzed and concentration values of cladribine were determined. The results were compiled and are summarized in the tables below (Tables V and VI). In these tables, the following definitions are applicable: $T_{max}$ is the time to reach maximum concentration in the plasma; $T_{1/2}$ is the half-life of cladribine in the plasma; $C_{MAX}$ is the maximum concentration of cladribine in the plasma; $AUC_{inf}$ is the area under the curve for the measured data from zero extrapolated to infinity; $AUC_t$ is the area under the curve for the measured data (from zero to the last time point); Geom Mean is the geometric mean; CV is the coefficient of variation (relative standard deviation); LL is the lower limit; UL is the upper limit.

Example 5

Clinical Study

Dose Response and Absolute Bioavailability

The objective of this study was to assess the systemic availability of cladribine after oral administration in two different fixed oral doses, in comparison with one fixed intravenous administration (reference formulation) in patients with MS (multiple sclerosis), and to evaluate the safety and tolerability of cladribine in this population.

This study was a 3 center, open-label, randomized, 3-way crossover single dose study using twenty-six patients with MS. Patients received randomly two different fixed oral doses (3.0 mg and 10.0 mg) and a fixed intravenous dose of 3.0 mg (administered as a 1 hour infusion). The three treatment days were separated by a drug-free interval of at least 5 days. In each treatment period blood samples were collected over a 24-hour period for evaluation of plasma cladribine.

The plasma concentrations of cladribine were measured by a HPLC/MS/MS method. Using this method the relationship between concentrations versus peak area ratios was found to be linear within the range of 100 pg/ml to 50,000 pg/ml for cladribine. The limit of quantification was 100 pg/ml. Analysis of samples was carried out in 16 runs. Except the first run (which had to be rejected because of equipment failure), all other runs could be accepted. No calibrator had to be excluded from fitting of the calibration curve and accuracy of each quality control sample met the GLP requirements.

858 clinical plasma samples were analyzed and concentration values of cladribine were determined. The results were compiled and are summarized in the tables below [TABLES VII through X]. In these tables, the following definitions are applicable: $T_{max}$ is the time to reach maximum concentration in the plasma; $T_{1/2}$ is the half-life of cladribine in the plasma; $C_{max}$ is the maximum concentration of cladribine in the plasma; $AUC_{inf}$ is the area under the curve for the measured data from zero extrapolated to infinity; $AUC_t$ is the area under the curve for the measured data (from zero to the last time point); Geom Mean is the geometric mean; CV is the coefficient of variation (relative standard deviation); LL is the lower limit; UL is the upper limit; $\sigma^2$ is the mean variance; $\sigma_B^2$ is the mean variance between subjects; $\sigma_W^2$ is the mean variance within subjects; $CV_T$ is the total coefficient of variation; and $CV_W$ is the coefficient of variation within subjects.

TABLE V

Summary Statistics for Pharmacokinetic Parameters for Cladribine Study Obtained via Non-Compartmental Analysis. (n = 12).

| Pharmacokinetic Parameter | 3.0 mg subcutaneous | | | 3 mg Tablet 1 | | | 3 mg Tablet 2 | | | 3 mg Capsule | | |
|---|---|---|---|---|---|---|---|---|---|---|---|---|
| | Geom Mean | Mean ± SD | CV** (%) | Geom Mean | Mean ± SD | CV** (%) | Geom Mean | Mean ± SD | CV** (%) | Geom Mean | Mean ± SD | CV** (%) |
| $T_{max}$ (hr) | N/A | .313 ± .113 | 36.2 | N/A | .521 ± .167 | 32.1 | N/A | 1.25 ± .839 | 67.1 | N/A | 2.25 ± .622 | 27.7 |
| $T_{1/2}$ (hr) | N/A | 6.69 ± 2.01 | 30.1 | N/A | 7.55 ± 2.50 | 33.1 | N/A | 6.73 ± 2.82 | 41.9 | N/A | 6.27 ± 2.31 | 36.9 |
| $C_{max}$ (pg/ml) | 23186 | N/A | 40.1 | 6597 | N/A | 24.7 | 5041 | N/A | 52.6 | 3818 | N/A | 36.8 |
| $AUC_{inf}$ (hr.pg/ml) | 57254 | N/A | 44.4 | 24936 | N/A | 28.8 | 21676 | N/A | 42.7 | 22604 | N/A | 39.5 |
| $AUC_t$ (hr.pg/ml) | 54725 | N/A | 43.8 | 23182 | N/A | 28.0 | 20063 | N/A | 42.1 | 20951 | N/A | 42.0 |

**CV = SD/mean for $T_{max}$ and $T_{1/2}$ and CV % geometric mean for $C_{max}$, $AUC_{inf}$ and $AUC_t$.

TABLE VI

Ratios of Oral to Subcutaneous Pharmacokinetic Parameters and Corresponding Two-Sided 90% Confidence Intervals for Cladribine Study (n = 12).

| Pharmacokinetic Parameter | 3 mg Tablet 1 | | 3 mg Tablet 2 | | 3 mg Capsule | |
|---|---|---|---|---|---|---|
| | Ratio* | LL, UL | Ratio* | LL, UL | Ratio* | LL, UL |
| $AUC_{inf}$ | 43.1 | 35.7, 52.1 | 38.4 | 31.8, 46.4 | 38.9 | 32.1, 47.0 |
| $AUC_t$ | 41.9 | 34.6, 50.8 | 37.2 | 30.7, 45.0 | 37.6 | 31.0, 45.5 |

*Ratios (dose normalized) and Corresponding 95% LL obtained via inverse transformation of log-transformed data.

TABLE VII

Summary Statistics for Pharmacokinetic Parameters for Cladribine Study
Obtained via Non-Compartmental Analysis (n = 26)

| | | | | Oral Administration | | | | | |
|---|---|---|---|---|---|---|---|---|---|
| | 3.0 mg IV infusion | | | 3.0 mg | | | 10.0 mg | | |
| Pharmacokinetic Parameter | Geom Mean | Mean ± SD | CV** (%) | Geom Mean | Mean ± SD | CV** (%) | Geom Mean | Mean ± SD | CV** (%) |
| $T_{max}$ (hr) | N/A | .817 ± .397 | 48.6 | N/A | .548 ± .300 | 54.8 | N/A | .558 ± .204 | 36.5 |
| $T_{1/2}$ (hr) | N/A | 6.50 ± 1.27 | 19.5 | N/A | 5.85 ± 1.18 | 20.2 | N/A | 5.60 ± 0.75 | 13.3 |
| $C_{max}$ (pg/ml) | 21425 | N/A | 27.6 | 5608 | N/A | 49.5 | 21242 | N/A | 50.5 |
| $AUC_{inf}$ (hr.pg/ml) | 58528 | N/A | 24.0 | 20159 | N/A | 35.0 | 76690 | N/A | 30.3 |
| $AUC_t$ (hr.pg/ml) | 56396 | N/A | 24.0 | 19166 | N/A | 36.9 | 74532 | N/A | 30.3 |

**CV = SD/mean for $T_{max}$ and $T_{1/2}$ and CV % geometric meand for $C_{max}$, $AUC_{inf}$ and $AUC_t$.

TABLE VIII

Ratios of Oral to I.V. Pharmacokinetic Parameters and
Corresponding Lower Limit (LL) for the one-sided 95%
Confidence Interval for Cladribine Study (n = 26)

| | Oral Administration | | | |
|---|---|---|---|---|
| Pharmacokinetic | 30.0 mg | | 10.0 mg | |
| Parameter | Ratio* | LL | Ratio* | LL |
| $AUC_{inf}$ | 34.5 | 31.7 | 39.1 | 35.9 |
| $AUC_t$ | 34.0 | 31.2 | 39.4 | 36.1 |

*Ratios (dose normalized) and Corresponding 95% LL obtained via inverse transformation of log-transformed data.

TABLE IX

Ratios and Corresponding two-sided 90% Confidence Intervals for
Cladribine Study (n = 26)

| Pharmacokinetic | 10.0 mg/3.0 mg | | |
|---|---|---|---|
| Parameter | Ratio* | LL | UL |
| $C_{max}$ | 112.6 | 95.1 | 1.33.3 |
| $AUC_{inf}$ | 113.3 | 104.2 | 123.3 |
| $AUC_t$ | 115.8 | 106.1 | 126.5 |

*Ratios (dose normalized) and Corresponding 90% CI obtained via inverse transformation of log-transformed data.

TABLE X

Variance components for Cladribine Study (n = 26)

| Source of variation | $C_{max}$ | $AUC_{inf}$ | $AUC_t$ |
|---|---|---|---|
| Between ($\sigma_B^2$) | .0380 | .0487 | .0492 |
| With ($\sigma_W^2$) | .1315 | .0330 | .0357 |
| TOTAL ($\sigma_B^2 + \sigma_W^2$) | .1695 | .0816 | .0849 |
| $CV_T$ (%) | 43.0 | 29.2 | 29.8 |
| $CV_W$ (%) | 37.5 | 18.3 | 19.1 |

Where PK parameters are dose-adjusted and $CV = \sqrt{\exp(\sigma^2)}$

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents thereof may be resorted to, falling within the scope of the invention claimed.

What is claimed is:

1. A complex cladribine-cyclodextrin complex which is an intimate amorphous admixture consisting of (a) an amorphous inclusion complex of cladribine with the amorphous cyclodextrin hydroxypropyl-β-cyclodextrin and (b) amorphous free cladribine associated with said amorphous cyclodextrin as a non-inclusion complex, said complex cladribine-cyclodextrin complex having a weight ratio of cladribine to said amorphous cyclodextrin of from about 1:10 to about 1:16.

2. The complex cladribine-cyclodextrin complex according to claim 1, saturated with cladribine.

3. The complex cladribine-cyclodextrin complex according to claim 1, wherein the weight ratio of cladribine to hydroxypropyl-β-cyclodextrin is about 1:14.

4. The complex cladribine-cyclodextrin complex according to claim 1, wherein the weight ratio of cladribine to hydroxypropyl-β-cyclodextrin is about 1:11.

5. The complex cladribine-cyclodextrin complex according to claim 1, wherein from about 30 to about 40 percent by weight of the cladribine is in the inclusion complex (a) and from about 70 to about 60 percent by weight of the cladribine is in the non-inclusion complex (b).

6. A pharmaceutical composition comprising a complex cladribine-cyclodextrin complex which is an intimate amorphous admixture consisting of (a) an amorphous inclusion complex of cladribine with the amorphous cyclodextrin hydroxypropyl-β-cyclodextrin and (b) amorphous free cladribine associated with said amorphous cyclodextrin as a non-inclusion complex, formulated into a solid oral dosage form, said composition comprising no significant amount of free crystalline cladribine therein, said composition having a weight ratio of cladribine to said amorphous cyclodextrin of from about 1:10 to about 1:16.

7. The pharmaceutical composition according to claim 6, wherein the complex cladribine-cyclodextrin complex is saturated with cladribine.

8. The composition according to claim 6, wherein the weight ratio of cladribine to hydroxypropyl-β-cyclodextrin is about 1:14.

9. The composition according to claim 6, wherein the weight ratio of cladribine to hydroxypropyl-β-cyclodextrin is about 1:11.

10. The composition according to claim 7, wherein the approximate molar ratio of cladribine to said amorphous cyclodextrin corresponds to a point located on the curve of a phase solubility diagram for saturated complex cladribine-cyclodextrin complexes, said curve defining complex saturated complexes of cladribine in varying concentrations of the cyclodextrin.

11. The composition according to claim 6, wherein from about 30 to about 40 percent by weight of the cladribine is in the inclusion complex (a) and from about 70 to about 60 percent by weight of the cladribine is in the non-inclusion complex (b).

12. A pharmaceutical composition according to claim 6 obtainable by a process comprising the steps of:
(i) combining cladribine and the amorphous cyclodextrin hydroxypropyl-β-cyclodextrin in water at a temperature of from about 45 to about 80° C. and maintaining said temperature for a period of from about 6 to about 24 hours;
(ii) cooling the resultant aqueous solution to room temperature;
(iii) lyophilizing the cooled solution to afford an amorphous product; and
(iv) formulating the amorphous product into a solid oral dosage form.

13. A pharmaceutical composition according to claim 12, wherein the process further comprises a filtration step following step (i) or (ii).

14. A pharmaceutical composition according to claim 12, wherein step (i) of the process is performed at a temperature of from about 45 to about 60° C.

15. A pharmaceutical composition according to claim 12, wherein step (i) of the process is performed at a temperature of from about 45 to about 50° C.

16. A pharmaceutical composition according to claim 14, wherein step (i) of the process is performed with stirring.

17. A pharmaceutical composition according to claim 16, wherein step (i) of the process is performed for a period of from about 6 to about 9 hours.

18. A pharmaceutical composition according to claim 12, wherein step (ii) of the process is performed for a period of from about 6 to about 9 hours.

19. A pharmaceutical composition according to claim 12, wherein step (iii) comprises an initial freezing stage in which the solution is cooled to from about −40 to about −80° C., and held at said temperature for a period of from about 2 to about 4 hours.

20. A pharmaceutical composition according to claim 19, wherein, in the initial freezing stage of step (iii), the solution is cooled to about −45° C.

21. A pharmaceutical composition according to claim 12, wherein 12.00 parts by weight of cladribine and 172.50 parts by weight of the hydroxypropyl-β-cyclodextrin are introduced in step (i) of the process.

22. A pharmaceutical composition according to claim 12, wherein 16.35 parts by weight of cladribine and 172.50 parts by weight of the hydroxypropyl-β-cyclodextrin are introduced in step (i) of the process.

23. A pharmaceutical composition according to claim 21, wherein 825 parts by volume of water are introduced in step (i) of the process.

24. A pharmaceutical composition according to claim 12, wherein the lyophilization step (iii) of the process comprises:
(a) an initial freezing stage in which the complexation solution is brought to from about −40° C. to about −80° C. for approximately 2 to 4 hours;
(b) a primary drying stage at about −25° C. for approximately 80 to 90 hours; and
(c) a secondary drying stage at about 30° C. for approximately 15 to 20 hours.

25. A pharmaceutical composition according to claim 24, wherein stage (a) of the lyophilization is conducted at about −45° C. for approximately 3 to 4 hours.

26. A pharmaceutical composition according to claim 24, wherein stage (b) of the lyophilization is conducted under a pressure of about 100 mTorr.

27. A pharmaceutical composition according to claim 12, wherein the formulation step (iv) of the process comprises blending the complex with magnesium stearate and compressing into tablets.

28. A pharmaceutical composition according to claim 27, wherein magnesium stearate is pre-mixed with sorbitol powder before blending with the complex.

29. A method for enhancing the oral bioavailability of cladribine comprising orally administering to a subject in need thereof a pharmaceutical composition comprising a complex cladribine-cyclodextrin complex which is an intimate amorphous admixture consisting of (a) an amorphous inclusion complex of cladribine with the amorphous cyclodextrin hydroxypropyl-β-cyclodextrin and (b) amorphous free cladribine associated with said amorphous cyclodextrin as a non-inclusion complex, formulated into a solid oral dosage form, said composition comprising no significant amount of free crystalline cladribine therein, said composition having a weight ratio of cladribine to said amorphous cyclodextrin of from about 1:10 to about 1:16.

30. The method according to claim 29, wherein the complex cladribine-cyclodextrin complex is saturated with cladribine.

31. The method according to claim 29, wherein the weight ratio of cladribine to hydroxypropyl-β-cyclodextrin is about 1:14.

32. The method according to claim 29, wherein the weight ratio of cladribine to hydroxypropyl-β-cyclodextrin is about 1:11.

33. The method according to claim 30, wherein the approximate molar ratio of cladribine to said amorphous cyclodextrin corresponds to a point located on the curve of a phase solubility diagram for saturated complex cladribine-cyclodextrin complexes, said curve defining complex saturated complexes of cladribine in varying concentrations of the cyclodextrin.

34. The method according to claim 29, wherein from about 30 to about 40 percent by weight of the cladribine is in the inclusion complex (a) and from about 70 to about 60 percent by weight of the cladribine is in the non-inclusion complex (b).

35. A method for the treatment of a condition selected from the group consisting of multiple sclerosis, rheumatoid arthritis and leukemia in a subject suffering from said condition comprising orally administering to said subject a pharmaceutical composition comprising a complex cladribine-cyclodextrin complex which is an intimate amorphous admixture consisting of (a) an amorphous inclusion complex of cladribine with the amorphous cyclodextrin hydroxypropyl-β-cyclodextrin and (b) amorphous free cladribine associated with said amorphous cyclodextrin as a non-inclusion complex, formulated into a solid oral dosage form, said composition comprising no significant amount of free crystalline cladribine therein, said composition having a weight ratio of cladribine to said amorphous cyclodextrin of from about 1:10 to about 1:16.

36. The method according to claim 35, wherein the complex cladribine-cyclodextrin complex is saturated with cladribine.

37. The method according to claim 35, wherein the condition is multiple sclerosis.

38. The method according to claim 35, wherein the weight ratio of cladribine to hydroxypropyl-β-cyclodextrin is about 1:14.

39. The method according to claim 25, wherein the weight ratio of cladribine to hydroxypropyl-β-cyclodextrin is about 1:11.

40. The method according to claim 35, wherein from about 30 to about 40 percent by weight of the cladribine is in the inclusion complex (a) and from about 70 to about 60 percent by weight of the cladribine is in the non-inclusion complex (b).

41. A process for the preparation of a complex cladribine-cyclodextrin complex as claimed in claim 1, which comprises the steps of:
  (i) combining cladribine and the amorphous cyclodextrin in water at a temperature of from about 45 to about 80° C. and maintaining said temperature for a period of from about 6 to about 24 hours;
  (ii) cooling the resultant aqueous solution to room temperature; and
  (iii) lyophilizing the cooled solution to afford an amorphous product.

42. A process according to claim 41, further comprising a filtration step following step (ii).

43. A process according to claim 41, wherein step (i) is performed at a temperature of from about 45 to about 60° C.

44. A process according to claim 41, wherein step (i) is performed at a temperature of from about 45 to about 50° C.

45. A process according to claim 43, wherein step (i) is performed with stirring.

46. A process according to claim 41, wherein step (i) is performed for a period of from about 6 to about 9 hours.

47. A process according to claim 41, wherein step (ii) is performed for a period of from about 6 to about 9 hours.

48. A process according to claim 41, wherein step (iii) comprises an initial freezing stage in which the solution is cooled to from about −40 to about −80° C., and held at said temperature for a period of from about 2 to about 4 hours.

49. A process according to claim 48, wherein, in the initial freezing stage of step (iii), the solution is cooled to about −45° C.

50. A process according to claim 41, wherein 12.00 parts by weight of cladribine and 172.50 parts by weight of hydroxypropyl-β-cyclodextrin are introduced in step (i).

51. A process according to claim 41, wherein 16.35 parts by weight of cladribine and 172.50 parts by weight of hydroxypropyl-β-cyclodextrin are introduced in step (i).

52. A process according to claim 50, wherein 825 parts by volume of water are introduced in step (i).

53. A process according to claim 41, wherein the lyophilization step (iii) comprises:
  (a) an initial freezing stage in which the complexation solution is brought to from about −40° C. to about −80° C. for approximately 2 to 4 hours;
  (b) a primary drying stage at about −25° C. for approximately 80 to 90 hours; and
  (c) a secondary drying stage at about 30° C. for approximately 15 to 20 hours.

54. A process according to claim 53, wherein stage (a) of the lyophilization is conducted at about −45° C. for approximately 3 to 4 hours.

55. A process according to claim 53, wherein stage (b) of the lyophilization is conducted under a pressure of about 100 mTorr.

* * * * *